(12) United States Patent
Qin et al.

(10) Patent No.: US 8,984,970 B2
(45) Date of Patent: Mar. 24, 2015

(54) METHOD AND APPARATUS FOR EVALUATING THE EFFICACY OF A CLEANING PRODUCT

(75) Inventors: Wendy Qin, Mason, OH (US); Thomas Schatto, Ingelheim-Grosswinternheim (DE); Randall Glenn Marsh, Hamilton, OH (US)

(73) Assignee: The Procter & Gamble Plaza, Cincinnati, OH (US)

( * ) Notice: Subject to any disclaimer, the term of this patent is extended or adjusted under 35 U.S.C. 154(b) by 341 days.

(21) Appl. No.: 13/531,809

(22) Filed: Jun. 25, 2012

(65) Prior Publication Data

US 2013/0340541 A1  Dec. 26, 2013

(51) Int. Cl.
*G01N 33/00* (2006.01)
*G01N 33/15* (2006.01)

(52) U.S. Cl.
CPC ................ *G01N 33/15* (2013.01); *G01N 33/00* (2013.01)
USPC .......................................................... 73/866

(58) Field of Classification Search
CPC ........ G01N 33/15; G01N 33/00; G01N 33/02
USPC .......................................................... 73/866
See application file for complete search history.

(56) References Cited

U.S. PATENT DOCUMENTS

| | | |
|---|---|---|
| 4,100,324 A | 7/1978 | Anderson et al. |
| 5,143,679 A | 9/1992 | Weber et al. |
| 5,147,343 A * | 9/1992 | Kellenberger ................ 604/368 |
| 5,518,801 A | 5/1996 | Chappell et al. |
| 5,628,097 A | 5/1997 | Benson et al. |
| 5,658,639 A | 8/1997 | Curro et al. |
| 5,914,084 A | 6/1999 | Benson et al. |
| 5,916,661 A | 6/1999 | Benson et al. |
| 6,114,263 A | 9/2000 | Benson et al. |
| 6,129,801 A | 10/2000 | Benson et al. |
| 6,383,431 B1 * | 5/2002 | Dobrin et al. ................. 264/154 |
| 6,673,358 B1 | 1/2004 | Cole et al. |
| 6,842,953 B2 | 1/2005 | Orlandi |
| 7,659,372 B2 | 2/2010 | Hood et al. |
| 7,744,531 B2 | 6/2010 | Marsh et al. |
| 7,972,986 B2 | 7/2011 | Barnholtz et al. |
| 8,158,689 B2 * | 4/2012 | Baker et al. ...................... 521/50 |
| 2003/0028165 A1 | 2/2003 | Curro et al. |
| 2004/0131820 A1 | 7/2004 | Turner et al. |
| 2004/0265534 A1 | 12/2004 | Curro et al. |

(Continued)

FOREIGN PATENT DOCUMENTS

WO   WO 2007/021844   2/2007

*Primary Examiner* — Hezron E Williams
*Assistant Examiner* — Rodney T Frank
(74) *Attorney, Agent, or Firm* — Sarah M. DeCristofaro; Abbey A. Lopez

(57) ABSTRACT

The product efficacy apparatus includes a roller having an outer surface and a test bed having a test surface. The roller may be affixed to a rotatable shaft having opposing end regions. The shaft may be rotatably connected to an arm at each end of the end regions of the shaft. Each arm is pivotally connected to a drive member that is rollingly connected to a stationary track. In operation, a cleaning product may be affixed to the outer surface of the roller. A controlled insult may be applied to the test surface. The arms pivot toward the test surface in order to direct the cleaning product on the outer surface of the roller into contact with the test surface. The drive members direct the roller over the controlled insult. The shaft rotates the roller over the test surface and the arms pivot the roller away from the test surface.

16 Claims, 9 Drawing Sheets

(56) References Cited

U.S. PATENT DOCUMENTS

| | | | |
|---|---|---|---|
| 2005/0136238 A1* | 6/2005 | Lindsay et al. | 428/304.4 |
| 2007/0148432 A1* | 6/2007 | Baker et al. | 428/304.4 |
| 2007/0286894 A1 | 12/2007 | Marsh et al. | |
| 2010/0274209 A1* | 10/2010 | Roe et al. | 604/378 |
| 2012/0251456 A1* | 10/2012 | O'Connor et al. | 424/9.2 |
| 2012/0252042 A1* | 10/2012 | Qin et al. | 435/8 |

* cited by examiner

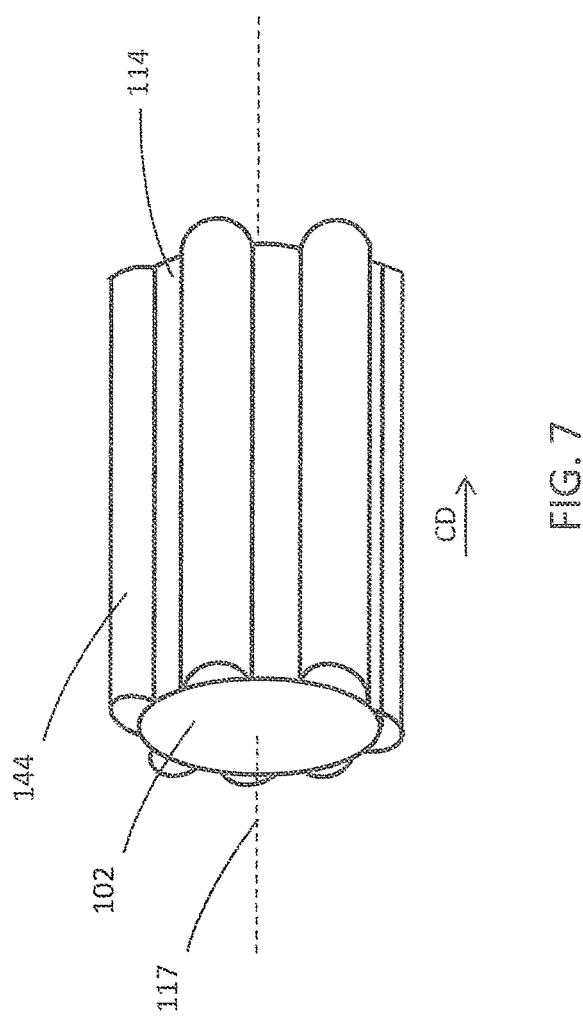

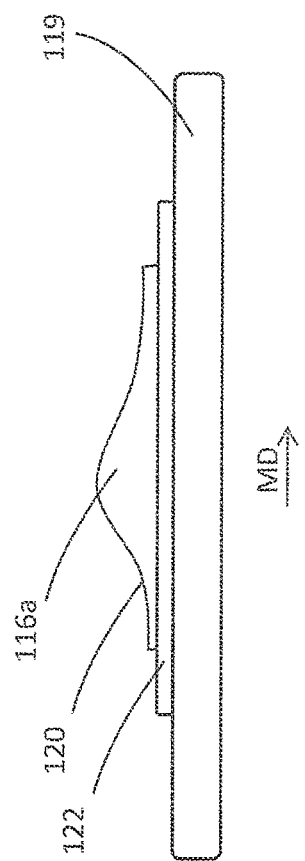

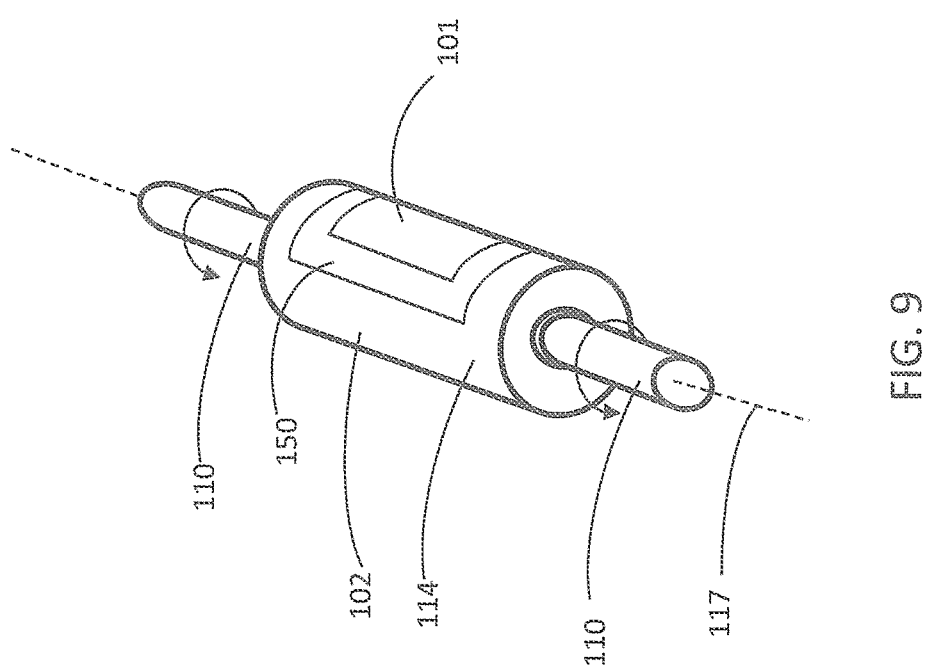

METHOD AND APPARATUS FOR EVALUATING THE EFFICACY OF A CLEANING PRODUCT

FIELD OF THE INVENTION

The present disclosure relates generally to methods and apparatuses for evaluating a cleaning product. In particular, the present disclosure relates to methods and apparatuses for evaluating the efficacy of a cleaning product.

BACKGROUND OF THE INVENTION

A variety of approaches exist for assessing the cleaning efficacy of a cleaning product. Approaches such as the identification and quantification of residual soil on the skin are known. For example, a known quantity of a known substance may be applied to skin, wiped with a cleaning product, and the substance transferred from the skin to the cleaning product quantified. Or, a known quantity of a known substance may be applied to a hard surface, wiped with a cleaning product, and the substance transferred from the skin to the cleaning product quantified. However, these approaches can be difficult to reproduce with consistency. In addition, it may be difficult to isolate and test one variable at a time when a test cannot be replicated with consistency.

In some instances, tests may be performed using a machine or may be performed by a human. While a human tester more closely mimics real cleaning conditions, results may vary from one human tester to another and from one test to another with the same human tester. A machine may be used to test the cleaning efficacy of a cleaning product by mimicking a blotting or wiping motion of a human hand. However, while machines may provide consistency and reproducibility from one test to another, blotting and/or wiping motions by a machine are unable to capture all aspects of a wiping motion of a human hand.

Thus, there remains a need for a reproducible test to evaluate the efficacy of a cleaning product that mimics the wiping motion of a human hand.

SUMMARY OF THE INVENTION

The present disclosure relates to a method for evaluating the efficacy of a cleaning product. The method may comprise the steps of: applying a controlled insult to a test surface of a test bed; providing a roller rotatable about an axis of rotation, the roller having an outer surface; affixing a cleaning product to the outer surface of the roller; positioning the cleaning product into contact with the test surface; moving the cleaning product in a machine direction over the controlled insult on the test surface; rotating the cleaning product over the test surface; lifting the cleaning product away from the test surface; and measuring the amount of controlled insult transferred from the test surface to the cleaning product.

The present disclosure may include an apparatus for evaluating the efficacy of a cleaning product. The apparatus may include a test bed, the test bed comprising a test surface. The apparatus may include a rotatable shaft having opposing end regions and a roller affixed to the rotatable shaft. The roller is located adjacent to the test surface and comprises an outer surface. The apparatus comprises an arm pivotally connected to each of the end regions of the rotatable shaft and a guide member rotatably connected to each of the end regions of the shaft. The apparatus also includes a drive member pivotally connected to each arm. The apparatus comprises a stationary track, wherein the guide members and drive members are configured to roll on the stationary track to move the roller in the machine direction over the test surface. The apparatus also includes a guide ramp positioned on each stationary track, wherein the guide members are configured to roll on and off of the guide ramps to pivot the arms.

BRIEF DESCRIPTION OF THE DRAWINGS

FIG. 7 is a schematic, perspective front view of an exemplary roller of a product efficacy apparatus.

FIG. 8 is a schematic, side elevation view of a test surface.

FIG. 9 is a schematic, perspective view of a roller having a material affixed to the outer surface and a cleaning product affixed to the material.

DETAILED DESCRIPTION OF THE INVENTION

The following term explanations may be useful in understanding the present disclosure:

The term "machine direction" ("MD") is used herein to refer to the direction that is parallel to the direction of travel of a roller of a product efficacy apparatus.

The term "cross direction" (CD) is used herein to refer to a direction that is not parallel with, and usually perpendicular to, the machine direction.

The term "controlled insult" is used herein to refer to a known quantity of a soil or composition.

The present disclosure relates to methods and apparatuses for evaluating the efficacy of a cleaning product by mimicking the wiping motion of a human hand. As discussed in more detail below, the product efficacy apparatus may include a roller rotatable about an axis of rotation and a test bed having a test surface located adjacent the roller. During the product efficacy evaluation, a cleaning product may be affixed to the roller and a controlled insult may be applied to the test surface. Drive members on the product efficacy apparatus may be configured to roll on a stationary track to move the roller and cleaning product in the machine direction over the controlled insult on the test surface. As discussed below, the product efficacy apparatus may be configured to mimic the wiping motion of a human hand. The product efficacy apparatus may also be configured to simulate a blotting motion.

Figure 1:
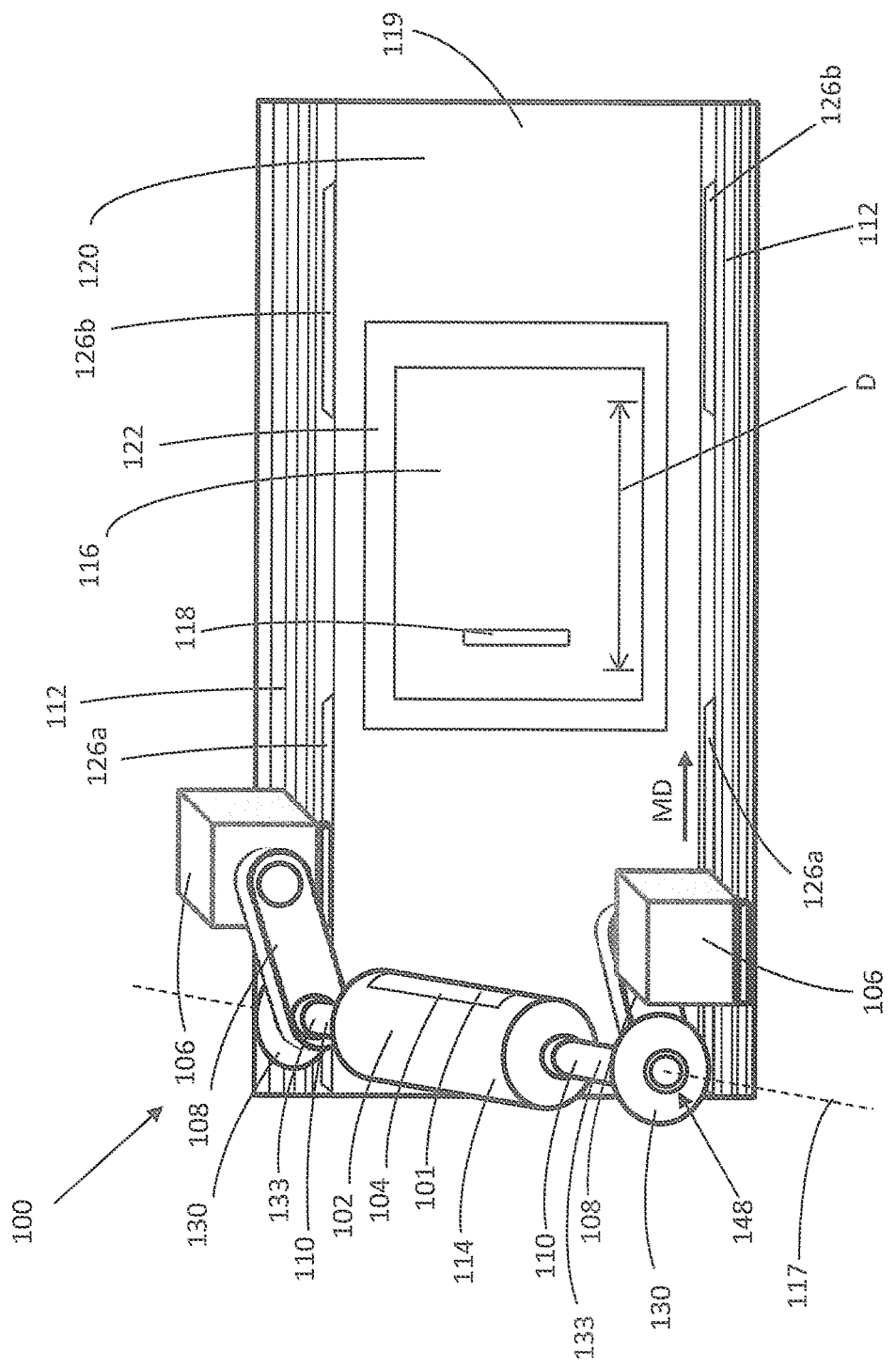
FIG. 1 is a schematic, perspective side view of an exemplary product efficacy apparatus.

An exemplary product efficacy apparatus 100 is shown in FIG. 1. The product efficacy apparatus 100 may include a roller 102 having an outer surface 114. The roller 102 may be affixed to a shaft 110 that is rotatable about the axis of rotation 117. The shaft 110 may be defined by opposing end regions 133. The roller 102 may be located adjacent to a test bed 119 having a test surface 120. The product efficacy apparatus 100 of FIG. 1 may include arms 108, one arm 108 rotatably connected to each of the end regions 133 of the shaft 110. The product efficacy apparatus 100 may also include guide members 130 that are rotatably connected to each of the end regions 133 of the shaft 110 and located adjacent to the arms 108. Each arm 108 may be pivotally connected to a drive member 106. The drive members 106 and the guide members 130 may rollingly contact the stationary tracks 112 in order to move the roller 102 in the machine direction MD over the test surface 120. The stationary tracks 112 may also include first and second guide ramps 126a and 126b, respectively, positioned for the guide members 130 to roll on.

Figure 2:
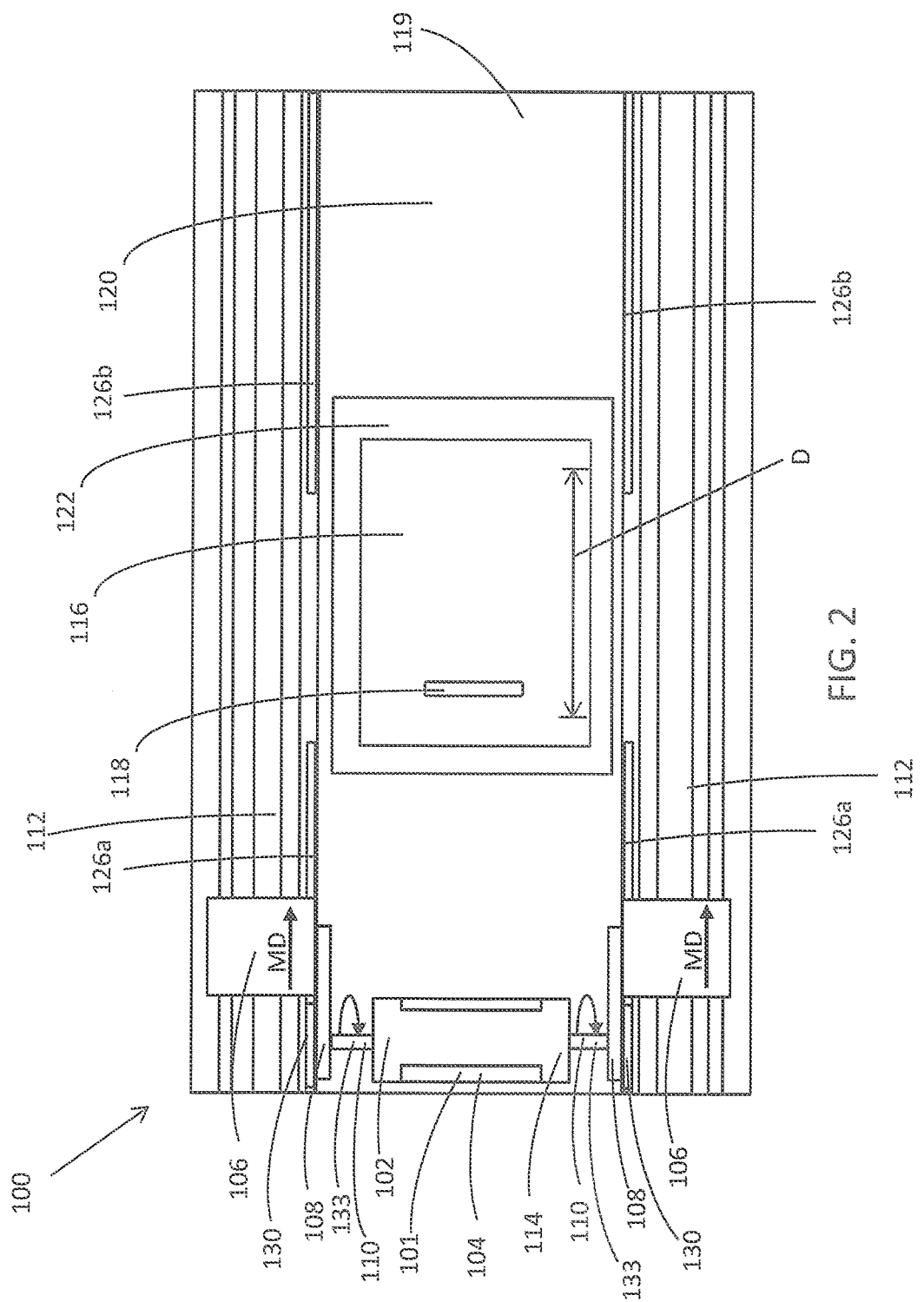
FIG. 2 is a schematic, plan view of an exemplary product efficacy apparatus before a product efficacy evaluation is performed.

FIG. 2 shows an exemplary product efficacy apparatus 100 before a product efficacy evaluation is performed. As shown in FIG. 2, a cleaning product 101, shown in the form of a substrate 104 for purposes of illustration, may be affixed to the outer surface 114 of the roller 102. A skin mimicking material 116 may be affixed to a mat 122 that is affixed to the test bed 119. The skin mimicking material 116 may form the test surface 120. A controlled insult 118 may be applied to the skin mimicking material 116.

Figure 3:
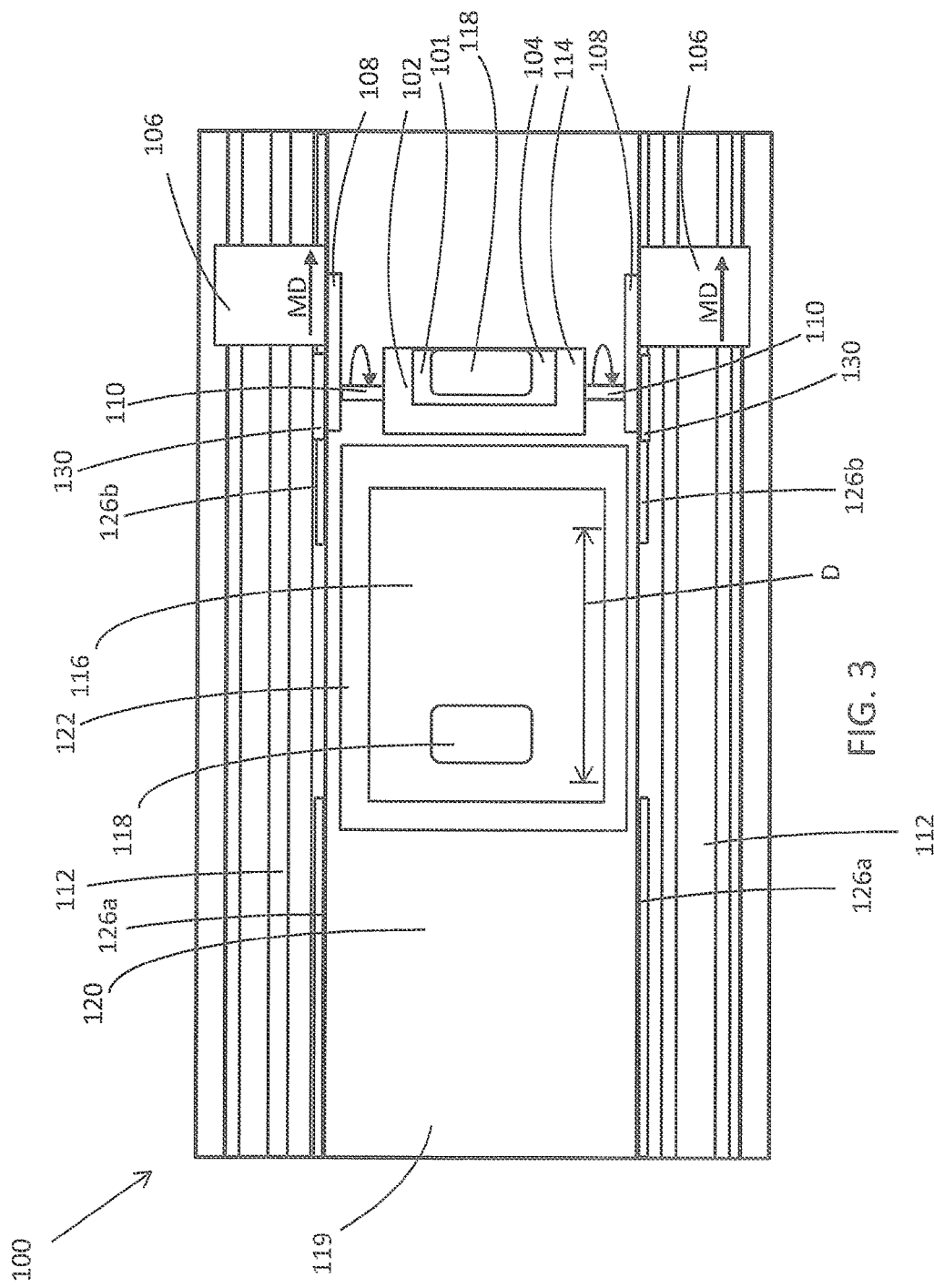
FIG. 3 is a schematic, plan view of an exemplary product efficacy apparatus after a product efficacy evaluation is performed.

As shown in FIGS. 1 and 3, in operation, the drive members 106 may roll on the stationary track 112 and the guide members 130 may rotate on the first guide ramps 126a in the machine direction MD. As the roller 102 approaches the controlled insult 118, the guide members 130 roll off of the first guide ramps 126a and onto the stationary track 112, which cause the arms 108 to pivot and move the substrate 104 on the roller 102 into contact with the test surface 120 and the controlled insult 118. The shaft 110 may rotate the roller 102 as the arms 108 pivot toward the test surface 120. The drive members 106 may then move the roller 102 in the machine direction MD over the controlled insult 118. The roller 102 may move in the machine direction MD for a distance D as shown in FIGS. 1-3. Additionally, the shaft 110 may rotate the substrate 104 over the skin mimicking material 116 as the roller 102 is moving in the machine direction MD. Next, the guide members 130 roll onto the second guide ramps 126b, causing the arms 108 to pivot away from the test surface 120 and move the roller 102 and the substrate 104 away from the test surface 120. The shaft 110 may rotate the roller 102 as the arms 108 pivot away from the test surface 120. Subsequently, the efficacy of the substrate 104 may be evaluated according to the methods disclosed herein. In addition, the skin mimicking material 116 and/or the cleaning product 101 may be used to evaluate the efficacy of the cleaning product 101.

Figure 4:
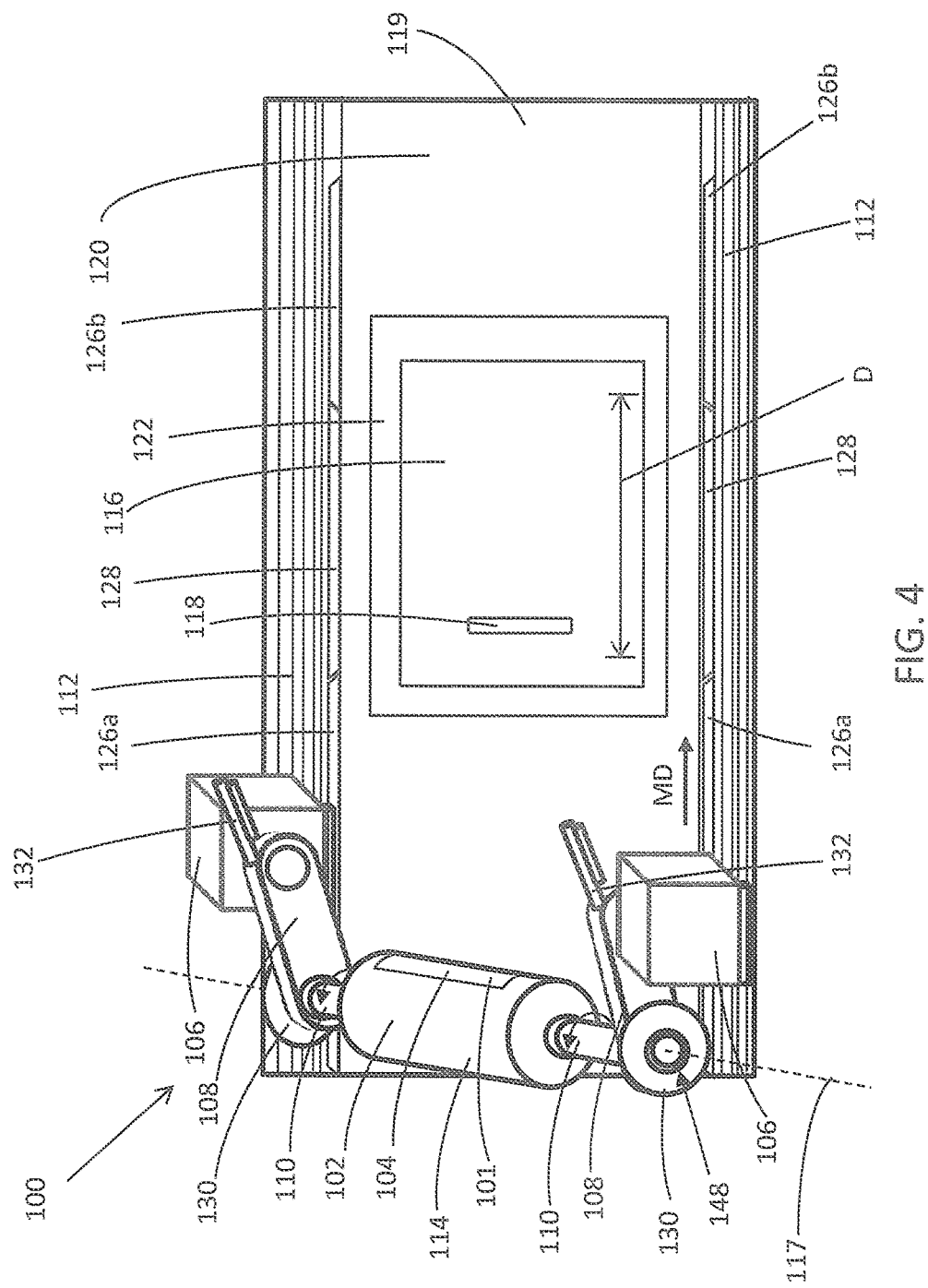
FIG. 4 is a schematic, perspective side view of an exemplary product efficacy apparatus including counterweights.

The product efficacy apparatus may be configured to adjust the pressure the roller applies to the test surface. For example, FIG. 4 shows a product efficacy apparatus 100 having counterweights 132 attached to the arms 108. The counterweights 132 may be affixed to the arm 108 in various ways known in the art, such as by clamping or taping the counterweights 132 to the arms 108. The counterweights 132 may be connected with each arm 108 such that each arm 108 acts as a lever and a connection 148 between the arm 108 and the drive member 106 acts as a fulcrum to balance the weight between the roller 102 and the counterweight 132. It is to be appreciated that increasing the weight added to the counterweight 132 will reduce the pressure applied by the roller 102 to the test surface 120.

With continuing reference to FIG. 4, the stationary track 112 may include guide bridges 128 to prevent the cleaning product 101 from being contaminated by the controlled insult 118 remaining on the test surface 120. The guide bridges 128 may be positioned between the first and second ramps 126a and 126b. The guide bridges 128 prevent the guide members 130 from rolling directly on the stationary track 112, which in turn prevents the arms 108 from moving toward the test surface 120. As such, each guide member 130 may roll over the second ramp 126b, the guide bridge 128, and the first ramp 126a to get from the position shown in FIG. 3 back to the starting position shown in FIG. 2.

Figure 5:
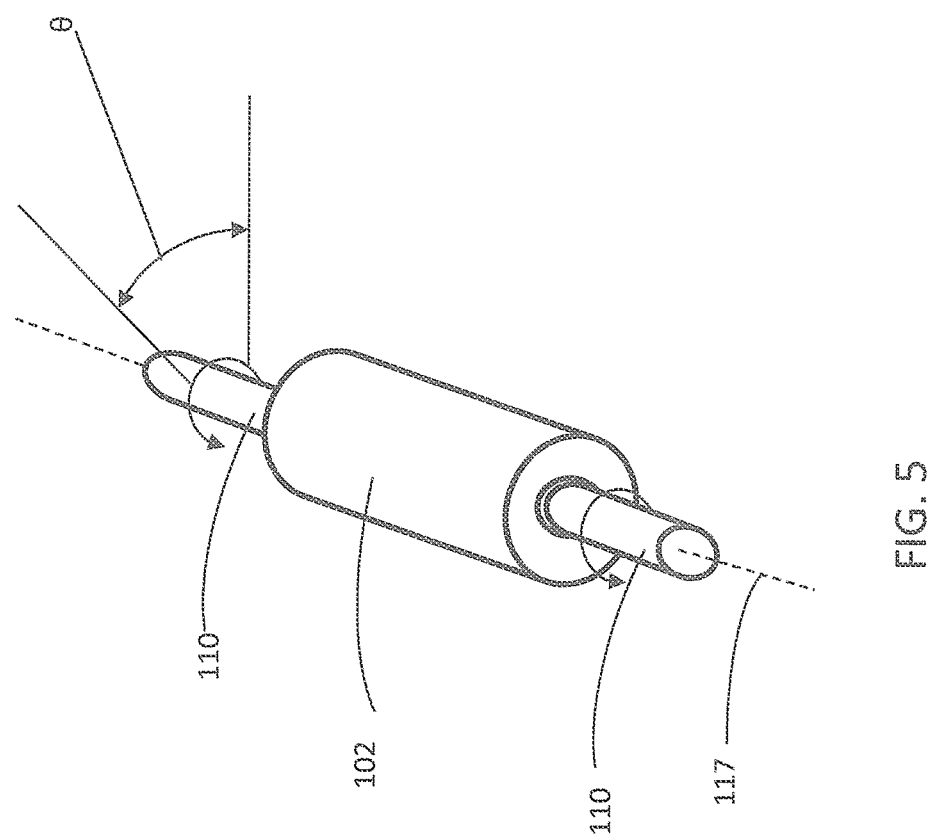
FIG. 5 is a schematic, perspective side view of a roller and shaft of a product efficacy apparatus.

As shown in FIG. 5, the shaft 110 may rotate the roller 102 at a rotation angle θ. As discussed above, the shaft 110 may rotate the roller 102 while the roller 102 is moving in the machine direction MD and/or while the arms 108 pivot the roller 102 toward and/or away from the test surface 120 of the test bed 119. The shaft 110 may be configured rotate the roller 102 at various rotation angles θ.

Figure 6:
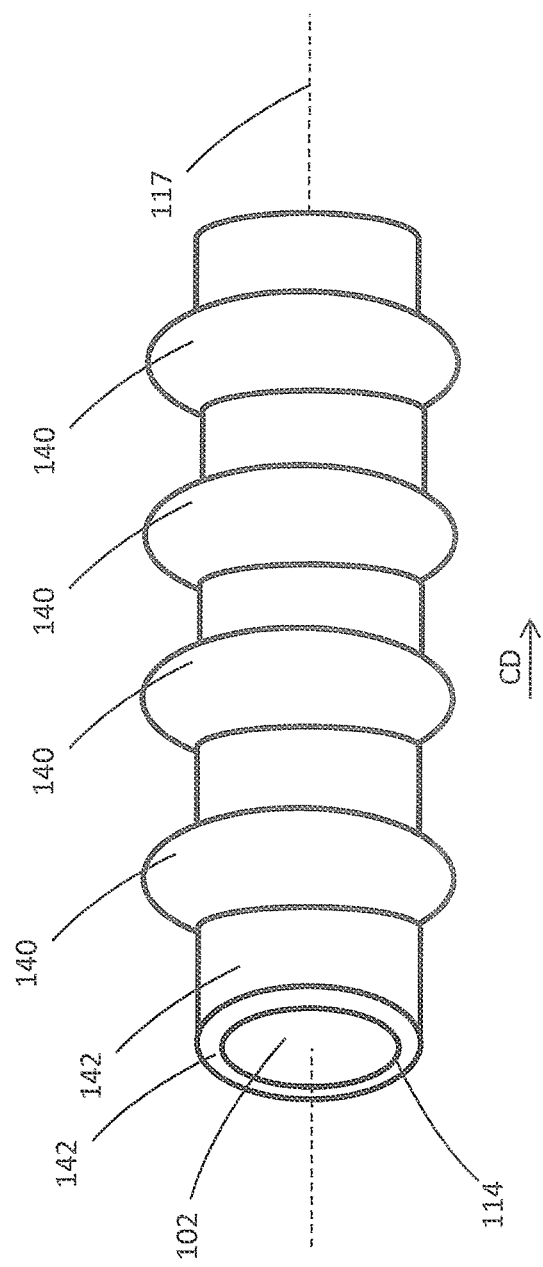
FIG. 6 is a schematic, perspective front view of an exemplary roller of a product efficacy apparatus.

FIG. 6 shows an exemplary roller 102 of a product efficacy apparatus 100 having a sleeve 142 attached to the outer surface 114 of the roller 102. As shown in FIG. 6, a roller 102 may include an outer surface 114. The outer surface 114 of the roller 102 may be covered with the sleeve 142 that may include a plurality of projections 140. FIG. 6 shows four projections 140 spaced apart in the cross direction CD. The projections 140 may more closely mimic the fingers of a human hand. While it is shown that the projections 140 are part of the sleeve 142, it is to be appreciated that projections 140 may be affixed to the outer surface 114 of a roller 102 in a variety of other ways. In another example, FIG. 7 shows a roller 102 having projections 144 extending from an outer surface 114 of the roller 102. The projections 144 may be affixed to the outer surface 114 of the roller 102 in a variety of ways, including adhesive. In this exemplary roller 102, the projections 144 may extend in the cross direction CD. The sleeve 142 may be made of a compressible material to mimic the compressibility of a human hand.

The test bed 119 may be covered with a skin mimicking material 116a and/or a mat 122 as shown in FIG. 8. The test bed 119 and the mat 122 may be substantially flat in the machine direction MD, while the skin mimicking material 116a may have a curved shape in the machine direction MD. It is to be appreciated that the skin mimicking material 116 shown in FIG. 8 forms the test surface 120. The test surface, the mat, and the skin mimicking material may have a variety of surface topographies. In some exemplary configurations, the skin mimicking material 116a may be affixed directly to the test bed 119.

The product efficacy apparatus may be configured in various ways. Referring back to FIG. 1, the roller 102 may be made of a variety of materials such as, for example, stainless steel or tool steel. While the roller 102 is shown in FIG. 1 as having a cylindrical shape, it is to be appreciated that the roller may have a variety of other shapes for simulating the motion of a human hand. The roller may be solid or may be hollow. The roller may have a relatively smooth outer surface or may have one or more projections extending from the outer surface in order to more closely mimic the shape of a human hand. Various objects may be attached to the roller to mimic various human body parts, including, for example, a hand, a buttocks, or a foot.

The roller may be used alone or may be used in combination with various other materials such as shown in FIG. 9. In some exemplary configurations, a material 150 may be affixed to the outer surface 114 of the roller 102. For example, the material may be a mat and/or a skin mimicking material. The material 101 may be configured to match the characteristics of a human hand, including, for example, compressibility and shape. As shown in FIG. 9, a cleaning product 101 may be affixed to the material 150 such that the material 150 is located between the roller 102 and the cleaning product 101. The material 150 may be substantially flat or may be contoured.

In some exemplary configurations, the test bed 119 and the test surface 120 may include a variety of materials. For example, the test bed may be made of glass, metal, tile, porcelain, wood, ceramic, marble, granite, vinyl, carpet, plastic, and combinations thereof. The test bed may be used alone, or may be covered with various other materials to form the test surface. For example, a skin or skin mimicking material may be affixed to the test bed. In some exemplary configurations, actual excised skin samples from animals or humans (live or from cadavers) may be used. Or, the test bed may be covered with a skin mimicking material such as, for example, polymers selected for some similarity to the skin of interest (whether human or animal, hairy or smooth, populated with sebaceous glands or not, etc.). For example, a polymer-based skin mimicking material may be selected for its compressibility or surface energy; or textured to simulate the outermost layer of a skin surface; or shaped to simulate the topography of a skin surface in situ; or coated to simulate the surface energy, coefficient of friction, polarity, or other properties of the skin of interest. In some exemplary configurations, the skin mimicking material may be contoured to mimic a portion or portions of a human body such as a baby's buttocks, for example. Some exemplary coatings are described, for example, in WO 2007/021844 to Belcher, et al. Exemplary skin mimicking materials may include D-C-Fix Film, Product No. 200-0907, manufactured by Konrad Hornschuch AG of Weissbach, Germany.

The test bed may include a mobile platform. For example, the test bed may include a mobile platform in the form of a conveyor, for example, for conducting successive tests. It is to be appreciated that the product efficacy apparatus may also comprise a plurality of rollers for conducting successive tests. In addition, in some exemplary configurations, multiple cleaning products may be affixed to the roller for conducting successive tests.

In some exemplary configurations, a mat may be affixed to the test bed. The mat may be made of a variety of materials such as, for example, foam or rubber. Exemplary mats may include Foam Rubber, Product No. 516783, distributed by Modulor GmbH of Berlin, Germany. The mat, skin, or skin mimicking materials may be affixed to the test bed in a variety of ways, including taping or fastening the materials to the test bed, for example.

The roller, arms, and drive members may be operated using a servo drive motor. It is to be appreciated that the servo drive motor may be programmed in various ways once the desired output parameters are known. The output parameters may include translational and rotational velocities of the roller, translational distance, and rotational angle. In some exemplary configurations, a product efficacy apparatus may include two or more rollers operatively connected with the shaft. In some exemplary configurations, the product efficacy apparatus may be operated, for example, by a computer and/or a robot.

As discussed above, the product efficacy apparatus may be configured to mimic the wiping motion of a human hand. The wiping motion of a human hand may include moving the cleaning product horizontally over a soiled surface, twisting the hand to transfer the soil from the surface to the cleaning product, and lifting the cleaning product containing the soil away from the surface. Referring back to FIG. 1, the roller 102 may be configured to first move down toward the test surface 120 of the test bed 119 by rolling the guide members 130 off of the first guide ramps 126a, which in turn causes the arms 108 to pivot down toward the test surface 120. To mimic the horizontal motion of a human hand, the roller 120 may move in the machine direction MD over the controlled insult 118 on the test surface 120. Next, to simulate a twisting motion of a human hand, the shaft 110 may be configured to rotate the roller 102 and the cleaning product 101 over the controlled insult 118 on the test surface 120 as the roller 102 is moving in the machine direction MD. The roller 102 may be restrained from rotating during at least a portion of the movement in the machine direction MD over the controlled insult 118. Subsequently, the product efficacy apparatus 100 may be configured to lift the roller 102, and thus the cleaning product 101, away from the test surface 120 by rolling the guide members 139 onto the second guide ramps 126b, which causes the arms 108 to pivot away from the test surface 120. In some exemplary configurations, the shaft 110 may be configured to rotate the roller 102 as the roller 102 lifts away from the test surface 120.

In some exemplary configurations, the product efficacy apparatus may be configured to simulate a blotting motion. The blotting motion of a human hand may include directing a cleaning product down toward a test surface of a test bed in a vertical direction, pressing the cleaning product against the test surface, and lifting the cleaning product away from the test surface in the vertical direction. Assuming that the test surface is on a horizontal plane, the product efficacy apparatus may be configured such that the roller moves vertically toward a test surface, applies a pressure to the test surface, and moves vertically away from the test surface.

It is to be appreciated that the product efficacy apparatus of the present disclosure may be used to assess the efficacy of various types of cleaning products, such as a substrate or an implement. A substrate may include a wipe or a cloth. As used herein, a wipe refers to a woven or non-woven substrate. A plurality of wipe substrates are known in the art, and disclosed, for example, in U.S. Pat. No. 6,673,358 to Cole et al. and U.S. Patent Publication No. 2007/0286894 to Marsh et al. "Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes. The fibers may be continuous fibers, staple fibers, or combinations thereof. The process for incorporating a fiber into a substrate may be selected based upon the sorts of component materials used and the desired properties of the substrate web. The nonwoven material may comprise one or more layers of fibrous assemblies, wherein each layer may include continuous fibers, coextruded fibers, non-continuous fibers, and combinations thereof. A suitable wipe may be constructed of any material or blend of materials which produces suitable flexibility, durability, and, if desired, liquid absorbency. Suitable fibers may be natural, cellulosic, wholly synthetic, or some combination of fibers. Natural or synthetic fibers may be treated or otherwise modified mechanically or chemically to provide desired characteristics or may be in a form that is generally similar to the form in which they can be found in nature.

In some exemplary configurations, particular combinations of fibers may be selected to provide desired characteristics. The fibers may be of one or more types, including different compositions or shapes of fibers. For example, fibers of certain lengths, widths, coarseness, shape or other characteristics may be combined in certain layers, or in distinct layers separate from each other. In some embodiments, suitable materials include viscose, polypropylene, polypropylene-viscose blends, polyethylene, polyester, rayon, cotton, cellulose, modified cellulose, pulp, and combinations thereof. The fibers may have core-and-sheath construction, and the core and sheath materials may be the same compositions or different compositions. The fibers may have inherent shapes, such as dog-bone, tri-lobal, multi-lobal, rounded, and delta. Combinations of fibers having different inherent shapes may be used. References to substrate "fibers", unless otherwise noted, include substrate components which are not true fibers, such as films, particles, yarns (or other collections of fibers), and the like. That is, a reference to a substrate fiber is not intended to limit the description to nonwoven substrates comprising true fibers.

The substrate materials may also be treated to improve the softness and texture thereof. The substrate may be subjected to various treatments, such as, but not limited to, physical treatment, such as hydro-molding, hydro-embossing, ring rolling, as described in U.S. Pat. No. 5,143,679 issued to Weber et al. on Sep. 1, 1992; structural elongation, as described in U.S. Pat. No. 5,518,801 issued to Chappell et al. on May 21, 1996; consolidation, as described in U.S. Pat. No. 5,914,084 issued to Benson et al. on Jun. 22, 1999; U.S. Pat. No. 6,114,263 issued to Benson et al. on Sep. 5, 2000; U.S. Pat. No. 6,129,801 issued to Benson et al. on Oct. 10, 2000 and U.S. Pat. No. 6,383,431 issued to Dobrin et al. on May 7, 2002; stretch aperturing, as described in U.S. Pat. No. 5,628,097 issued to Benson et al. on May 13, 1997; U.S. Pat. No. 5,658,639 issued to Curro et al. on Aug. 19, 1997 and U.S. Pat. No. 5,916,661 issued to Benson et al. on Jun. 29, 1999; differential elongation, as described in US Publication No. 2003/0028165A1 published on Feb. 6, 2003 by Curro et al.; and other solid state formation technologies as described in U.S. Publication No. 2004/0131820A1 published on Jul. 8, 2004 by Turner et al. and U.S. Publication No. 2004/0265534A1 published on Dec. 30, 2004 by Curro et al., zone activation, pressure bonding, needlepunching, airlaying, tufting, compaction, and the like; chemical treatment, such as, but not limited to, rendering part or all of the substrate hydrophobic, and/or hydrophilic, or increasing the hydrophobicity or hydrophilicity, and the like; thermal treatment, such as, but not limited to, thermal-embossing, softening of fibers by heating, thermal bonding and the like; and combinations thereof. Without being bound by theory, it is believed that a textured substrate may facilitate removal of bodily exudates or other soils by improving the ability to grip or otherwise lift the soils from the skin during cleansing. Other suitable substrates include coform substrates, such as described in U.S. Pat. No. 4,100,324 to Anderson et al., substrates formed by hydrodynamic needling, as described in U.S. Pat. No. 6,842,953 to Orlandi, and the substrates described in U.S. Pat. No. 7,972,986 to Barnholtz et al.

A wipe may be wet or dry. A dry wipe refers to a wipe with no aqueous lotion or wetting liquid added for cleaning or transferring substances between the wipe and a surface. A dry wipe may be coated or impregnated with anhydrous compounds. A dry wipe may also comprise cleaning actives that have been substantially dried onto the wipe or the wipe fibers and that remain in or on the wipe until the wipe is wetted. A dry wipe may be wetted prior to use, as by exposing the wipe to water or another solution, or a dry wipe may be wetted during use, as by exposing the wipe to urine, menses, or feces with a high fluid content. It should be understood that a dry wipe may, nonetheless, contain a small amount of moisture, such as less than 150% or 100% liquid by weight of liquid to weight of substrate. Exemplary, non-limiting dry wipes include tissues, toilet paper, napkins, and paper towels. A wet wipe may comprise water or an aqueous lotion. Many suitable lotions are known and new lotions are regularly proposed for varied purposes, including cleaning, treating, or refreshing a surface. For example, a wet wipe may comprise a lotion for the removal of soils; or for transferring compounds to improve the health, condition, or appearance of skin; or for creating a feeling or perception of coolness, warmth, tightening, relaxation, or the like. A wet wipe may contain, for example, 250% to 600% liquid by weight of liquid to weight of substrate.

The substrate may have a basis weight between about 15, 30, 40 or 45 grams/m$^2$ and about 65 or 75 grams/m$^2$ (gsm). A cloth refers to a woven or non-woven substrate having a basis weight greater than 80 gsm, such as a washcloth or a towel. A wipe refers to a woven or nonwoven substrate having a basis weight less than 80 gsm. A wipe may have a basis weight less than 75 gsm, or less than 65 gsm. One exemplary substrate may be a carded nonwoven comprising a 40/60 blend of viscose fibers and polypropylene fibers having a basis weight of 58 gsm as available from Suominen of Tampere, Finland as FIBRELLA™ 3160. Another exemplary material may be FIBRELLA™ 3100 which is a 62 gsm nonwoven web comprising 50% w/w 1.5 denier polypropylene fibers and 50% w/w 1.5 denier viscose fibers. Another suitable material for use as a substrate may be SAWATEX™ 2642 as available from Sandler AG of Schwarzenbach/Salle, Germany. Yet another suitable material for use as a cloth may have a basis weight of from about 40 gsm to about 200 gsm and have a 20/80 blend of viscose fibers and polypropylene fibers. The cloth may also be a 60/40 blend of pulp and viscose fibers.

An implement refers to any other device for cleaning, treating, or applying a composition to the skin or other surfaces, such as a "pouf" (sometimes called a gauze sponge or "scrubbie"); an absorbent article including, for example, a diaper, an incontinence pad, and feminine care pad; a sponge; a brush (power or manual); a loofah; a stick; various applicators such as, for example, cosmetic applicators; or cotton balls or wool (whether made of cotton or an alternative fiber); and combinations thereof.

In some exemplary configurations, the cleaning product may be arranged in various configurations. For example, a cleaning product may be affixed to the test surface of the test bed and a controlled insult may be applied to the roller. In another exemplary configuration, a first cleaning product may be affixed to the roller and a second cleaning product may be affixed to the test surface of the test bed.

The product efficacy apparatus may be used to test the efficacy of cleaning products having various thicknesses. For example, the product efficacy apparatus may be used to test the efficacy of a wipe having a thickness of less than 1 millimeter. The product efficacy apparatus may be used to evaluate cleaning products thicker than 1 millimeter such as various cloths and implements.

A cleaning product may be pre-treated with a composition, or may be used in combination with a composition. A composition may refer to a cleansing composition or a treatment composition. A cleansing composition, which may include water, may refer to a composition for the removal of soils, whether foreign or naturally occurring (such as skin oils). Cleansing compositions may include soaps, surfactants, or oils to help solubilize soils and remove the soils from the skin. Treatment compositions may comprise ingredients to maintain or improve the health, appearance, or feel of skin. Treatment compositions may comprise functional components including, but not limited to, emollients, moisturizers, cosmetics, vitamins, medications (e.g., for the prevention or reduction of acne), sunscreens, colorants, or combinations thereof. Some compositions may be both a cleansing composition and a treatment composition. For example, a wet wipe may comprise a lotion composition, the lotion composition comprising water, surfactants, and moisturizers.

A controlled insult may include, for example, a soil or a composition. The controlled insult may be liquid, solid, or a paste. The soil may include real or artificial soils, such as, for example, body exudates, household soils, household wastes, outdoor soils, and combinations thereof. Body exudates may include, for example, feces, menses, urine, nasal exudates, oral exudates, and vomitus. Household soils may include: foods such as, for example, cheeses, meats, fruits, vegetables, sauces, comminuted pastas and eggs; food wastes; beverages such as, for example, coffee, tea, soda, fruit juice, vegetable juice, milk, and fruit drinks; and the like. Outdoor soils may include, for example, paint, crayons humus, mud, dirt, and snow. Artificial soils, such as artificial feces, may have solid components, including dried vegetable(s), fiber, yeast, yeast derivatives, and/or fatty acids. The artificial soil may also have liquid components, which may include water, a preservative, and/or a mucus material. The artificial soil properties may be adapted by modifying the water content of the artificial soil. Artificial soil texture, including hardness and adhesive force to a standard test surface, may be modified by varying the water content of the artificial soil. In general, adding less water will make a firmer artificial soil, and adding more water will make a runnier and/or softer (lower hardness) artificial soil. It is to be appreciated that the water content of the artificial soil may affect the adhesive force of the soil to the test surface. Some exemplary artificial feces are described, for example, in U.S. application Ser. No. 13/421,925, filed on Mar. 16, 2012. Exemplary artificial menses are described in U.S. Pat. No. 7,659,372 B2.

Various quantities of a controlled insult may be applied to the test surface. For example, the amount of controlled insult applied to the test surface may be in the range of 0.1 to 25 grams. However, more or less controlled insult may be used. The controlled insult may be applied to the test surface in various shapes and configurations to mimic real soil conditions on a surface. In some exemplary configurations, the controlled insult may be delivered by a cleaning product. For example, the controlled insult may be applied to a cleaning product and the cleaning product containing the controlled insult may be affixed to the roller or the test surface of the test bed.

Measuring the efficacy of a cleaning product may be a useful metric in designing a cleaning product for cleaning and/or improving the condition of a surface, such as skin, for example. For example, mechanical or chemical properties of a cleaning product may be tested using the product efficacy apparatus. Mechanical properties to be tested may include, for example, strength, durability, basis weight, absorbency, texture, materials, composition transfer, thickness, resiliency, and combinations thereof. Chemical properties may include composition transfer and cleaning efficacy. In addition, a variety of test conditions may be analyzed. Test conditions may include soil characteristics and wiping conditions such as wiping pressure, wiping distance, rotational angle, and wiping speed.

The product efficacy apparatus may be configured to evaluate the efficacy of a cleaning product under a variety of conditions. For example, efficacy of a cleaning product may be tested under different times, pressures, velocities, rotation angles, and distances. In some exemplary configurations, it may be useful for test conditions to mimic real wiping conditions of a human hand. For example, it may be desirable for the pressure applied by the roller to the test surface to be in the range of the wiping pressures applied by a human hand to a surface. For example, the pressure applied by the roller to the test surface may be in the range of 0.1 to 10 pounds per square inch (psi), or in the range of 0.5 to 5 psi. In some exemplary configurations, it may be useful to test the efficacy of a cleaning product under various pressures. The roller may be configured to apply a constant pressure to the test surface as the roller moves in the machine direction. As discussed above, the pressure may be adjusted by attaching counterweights to the arms of the product efficacy apparatus. In other exemplary configurations, the pressure may be adjusted using a computer.

In addition, the translational velocity at which the roller moves in the machine direction over the test surface may be in the range of 0.1 to 5 centimeters per second (cm/s), or in the range of 0.5 to 2 cm/s. In some exemplary configurations, the rotational velocity at which the roller rotates over the test surface may be in the range of 0.1 to 5 cm/s, or in the range of 0.5 to 2 cm/s. It may be useful to test the efficacy of a cleaning product at different translational and rotational velocities. In addition, it may be useful to test the efficacy of a substrate over various wiping distances, D. The distance, D, the roller translates in the machine direction over the test surface may be in the range of 10 to 200 millimeters.

In some exemplary configurations, the product efficacy evaluation may be conducted under a variety of environmental conditions. For example, it may be useful to conduct the product efficacy evaluation at room temperature. In addition, it may be useful to conduct the product efficacy evaluation at or near the body temperature of a human or animal. Or, it may be useful to conduct the product efficacy evaluation at warmer or colder temperatures. In some exemplary configurations, a product efficacy evaluation may be conducted at various humidity levels. In other exemplary configurations, a product efficacy evaluation may be conducted under an applied air flow.

The product efficacy apparatus may be configured to rotate the roller at various rotation angles, $\theta$. For example, in some exemplary configurations, the roller may rotate at a rotation angle, $\theta$, of between about 15 to about 180 degrees. It may be useful to test the efficacy of a cleaning product over various rotation angles. As discussed above, the roller may rotate as the roller translating in the machine direction and/or as the roller is lifting away from the test surface. It may also be useful to test the efficacy of a cleaning product over various rotation angles while the roller is translating in the machine direction and/or while the roller is lifting away from the test surface.

In some exemplary configurations, it may be useful to test the efficacy of a substrate as it relates to the directional orientation of the fibers of a substrate relative to the movement of the roller. The fibers of a substrate may be substantially oriented in a single direction. In some exemplary configurations, the substrate may be affixed to the roller such that the fibers may be substantially oriented in the machine direction, cross direction, or in a diagonal direction relative to the translational movement of the roller in the machine direction. It may be useful to test the efficacy of a substrate in various fiber orientations.

The product efficacy apparatus may be used, for example, to test one or both surfaces of a cleaning product. For example, a cleaning product may have a first surface and a second surface. In some exemplary configurations, the cleaning product may be positioned on the roller such that the first surface contacts the outer surface of the roller and the second surface faces the controlled insult on the test surface. It is to be appreciated that the first surface and the second surface of the cleaning product may have different characteristics. For example, the first and second surfaces of the cleaning product may have, for example, different textures, treatments, compositions, and combinations thereof. It may be useful to compare the efficacy of the first surface to the efficacy of the second surface in order to evaluate the efficacy of different surface characteristics and compositions. In some exemplary configurations, two identical cleaning products may be used to evaluate the efficacy of the first surface and the second surface. In some exemplary configurations, a controlled insult of known mass may be applied to a test surface. A cleaning product may be affixed to the product efficacy apparatus such that the first surface is in contact with the roller and the second surface is facing the controlled insult on the test surface. The product efficacy apparatus may be used to wipe the controlled insult from the test surface. The amount of controlled insult transferred from the test surface to the second surface of the cleaning product may be evaluated. In another test, a controlled insult of known mass may be applied to the test surface. A second cleaning product, which is identical to the first cleaning product, may be affixed to the product efficacy apparatus such that the second surface is in contact with the roller and the first surface is facing the controlled insult on the test surface. The product efficacy apparatus may be used to wipe the controlled insult with the cleaning product. The amount of controlled insult transferred from the test surface to the first surface of the cleaning product may be evaluated. The efficacy of the first surface may be compared to the efficacy of the second surface of the cleaning product.

The product efficacy apparatus may also be used to evaluate the efficacy of a cleaning product arranged in various configurations. For example, a human user may hold a cleaning product substantially flat in the user's hand, or may fold or bunch the cleaning product to wipe a surface with the cleaning product. In some exemplary configurations, the cleaning product may be positioned substantially flat on the roller, may be affixed to the roller in a folded orientation, or may be bunched, wrinkled, or crumpled, and then affixed to the roller. It may be useful to test the efficacy of a cleaning product that is affixed to the roller in various configurations.

The product efficacy apparatus may be useful, for example, for assessing the efficacy of a cleaning product over multiple hand wiping evaluations. For example, it may be necessary to wipe a surface such as skin, for example, multiple times with the same cleaning product in order to remove all or substantially all of the soil from the surface. Using the product efficacy apparatus, a single controlled insult may be wiped once, twice, or multiple times in order to more completely remove the controlled insult from the test surface. The efficacy of the cleaning product may be evaluated after each wipe by the cleaning product by measuring the amount of controlled insult remaining on the test surface, or by quantifying the amount of soil on the cleaning product.

The product efficacy apparatus may be used to evaluate whether soil soaks through a cleaning product. In use, a soil may soak through a cleaning product such that the soil comes into contact with the user's hand. It may be useful to quantify the amount of soil that soaks through a particular cleaning product. In some exemplary configurations, a controlled insult of known mass may be applied to a test surface. The product efficacy apparatus may be used to wipe a cleaning product over the controlled insult. The amount of controlled insult that soaks through to the surface of the wipe that is in contact with the roller may be quantified using the techniques disclosed herein.

The product efficacy apparatus may be used to test the absorbency of a cleaning product. For example, a liquid or semi-liquid controlled insult may be applied to the test surface. A cleaning product may be affixed to the outer surface of the roller. The product efficacy apparatus may be used to wipe the cleaning product over the controlled insult on the test surface. The amount of controlled insult that was absorbed by the cleaning product may be quantified.

In some exemplary configurations, the product efficacy apparatus may be used to evaluate the retention of the controlled insult to the cleaning product. For example, a cleaning product may be used to clean a surface containing a controlled insult. The cleaning product containing the controlled insult from the surface may be affixed to the roller of the product efficacy apparatus. The cleaning efficacy apparatus may be used to wipe the cleaning product over a clean test surface. The cleaning efficacy apparatus may be configured to apply various pressures to the test surface. The cleaning product or the test surface may be evaluated to quantify the amount of controlled insult retained on the cleaning product. In some exemplary configurations, the cleaning product may be affixed to the test surface.

The product efficacy apparatus may also be used to evaluate the cleaning and treatment effects of a composition. For example, in the case of a cleansing composition, the product efficacy apparatus may be used to quantify the cleaning efficacy of a cleaning product with different cleaning compositions. In addition, the product efficacy apparatus may be used to quantify the amount of cleaning or treatment composition that is transferred from the cleaning product to the test surface. In some exemplary configurations, it may be useful to test a cleaning product comprising a composition over multiple wipes. It is to be appreciated that the cleaning composition transferred to the test surface after a first wiping simulation may help the cleaning product remove the controlled insult from the test surface during subsequent wiping simulations.

In some exemplary configurations, it may be useful to quantify the amount of lotion or composition transferred from the cleaning product to the test surface. It may be useful to evaluate the transfer of lotion or composition from the cleaning product to the test surface without applying a controlled insult to the test surface. For example, skin mimicking material may be affixed to the test surface. A cleaning product may be affixed to the roller such that the first surface is in contact with the roller and the second surface is facing the test surface. The cleaning product may comprise a cleansing and/or treatment composition on at least the second surface. The product efficacy apparatus may be used to wipe the cleaning product over the skin mimicking material on the test surface. The amount of treatment and/or cleansing composition transferred from the cleaning product to the skin mimicking material may be quantified. In addition, the dimensions and uniformity of the composition on the test surface may be measured to evaluate how well the cleaning product coats the test surface.

In some exemplary configurations, the efficacy of an implement may be evaluated. For example, an implement may be affixed to the outer surface of the roller. It is to be appreciated that the implement may be affixed to the outer surface of the roller in a variety of ways such as, for example, taping, clamping, or bolting. While the outer surface of the roller may be a substantially smooth, the implement may have a variety of shapes such that the implement projects from the outer surface of the roller.

In some exemplary configurations, the roller may be configured to apply a liquid composition to a cleaning product affixed to the outer surface of the roller. For example, the roller may be substantially hollow and may be capable of holding liquid. The liquid may release from the roller by applying pressure to the outer surface of the roller. In some exemplary configurations, a liquid may be pumped through the roller, out of the outer surface of the roller, and to a cleaning product affixed to the roller. In some exemplary configurations, it may be useful to wipe a single controlled insult multiple times, each time using a clean cleaning product. A single cleaning product may be affixed to the outer surface of the roller. A skin mimicking material and/or a mat may be affixed to the test surface and a controlled insult may be applied to the skin mimicking material. The product efficacy apparatus may be used to wipe the cleaning product with the controlled insult on the test surface. A guide bridge may be used to return the product efficacy apparatus to the starting position. The cleaning product may be removed from the roller. A second cleaning product may be attached to the roller and the product efficacy apparatus may be used to wipe the same controlled insult for a second time with the second cleaning product. These steps may be repeated in order to wipe the controlled insult multiple times with multiple wipes. The amount of controlled insult transferred from the test surface to each cleaning product may be quantified.

In some exemplary configurations, multiple cleaning products may be affixed to the outer surface of the roller at one time. In some exemplary configurations, the cleaning products may be affixed to the roller such that as the roller rotates over the test surface, each subsequent cleaning product wipes over a controlled insult on the test surface. In another exemplary configuration, multiple cleaning products may be affixed on the roller the cross direction, such that the cleaning products are evaluated at one time.

The efficacy of a cleaning product may be quantified using visual inspection techniques. Visual inspection may include inspection under typical lighting conditions, or may be conducted under black light, or by colored light imaging, to visually demonstrate the residual soil and/or composition on the test surface after the wiping evaluation. For example, a controlled insult of known mass may be applied to a test surface. The product efficacy apparatus may be used to wipe a cleaning product over the controlled insult. In some examples, the residual controlled insult may be difficult or impossible to see under typical lighting conditions (e.g., standard fluorescent lighting, standard incandescent lighting, sunlight). Thus, a controlled insult such as, for example, artificial feces which fluoresces under a given lighting condition, such as red light, or blue light, or green light, or black light, may be used when the residual controlled insult would not normally be visually observable under typical lighting conditions with the unaided human eye. The controlled insult, for example, may include a marker that fluoresces under a given lighting condition. The amount of controlled insult remaining on the test surface may be quantified by visual inspection for the marker. Exemplary markers include GloGerm, which is manufactured by GloGerm Company of Moab, Utah. Exemplary natural fluorescent markers that may be used with the controlled insult include a tomato product, yeast powder, peanut butter, and mustard sauce, for example. Various other markers may be used for visualizing residual controlled insult, including, for example, proteins, DNA, and carbohydrates. Exemplary fluorescence imaging systems include the FluorChem 8800, manufactured by Protein-Simple of Santa Clara, Calif.

The efficacy of a cleaning product may be evaluated by tracking the presence of a biomarker on the test surface. Exemplary biomarkers include adenosine triphosphate, which is described in U.S. patent application Ser. No. 13/421,925, filed Mar. 16, 2012.

Other analytical methods for quantifying the amount of soil on the test surface or the cleaning product are well known and any suitable method may be used. Gravimetric analysis may be used to evaluate the transfer of a controlled insult from a test surface to a cleaning product and may also be used to evaluate the transfer of a controlled insult from a cleaning product to a test surface. In some exemplary configurations, a controlled insult of known mass may be applied to a test surface. The product efficacy apparatus may be used to wipe a cleaning product over the controlled insult. The cleaning product may be weighed before and after wiping the controlled insult. The difference between the mass of the cleaning product after wiping the controlled insult and the mass of the cleaning product before wiping the controlled insult can be attributed to the soil (from the controlled insult) that was removed by the cleaning product. In another exemplary configuration, a skin mimicking material may be used as the test surface. A known mass of a controlled insult may be applied to the skin mimicking material. The skin mimicking material containing the controlled insult may be weighed and then affixed to the test bed. The product efficacy apparatus may be used to wipe a cleaning product over the controlled insult. The skin mimicking material may be removed from the test bed and weighed after wiping the controlled insult. The difference between the mass of the skin mimicking material before and after being wiped by the cleaning product may be attributed to the soil removed by the cleaning product. An exemplary procedure for gravimetric analysis of the removal of soils from skin is described, for example, in U.S. Pat. No. 7,744,531 to Marsh, et al.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating the efficacy of a cleaning product, the method comprising:
   applying a controlled insult to a test surface of a test bed;
   providing a roller rotatable about an axis of rotation, the roller having an outer surface;
   affixing a cleaning product to the outer surface of the roller;
   positioning the cleaning product into contact with the test surface;
   moving the cleaning product in a machine direction over the controlled insult on the test surface;
   rotating the cleaning product over the test surface; wherein the steps of moving the cleaning product in the machine direction over the controlled insult and rotating the cleaning product over the test surface occur simultaneously;
   lifting the cleaning product away from the test surface; and measuring the amount of controlled insult transferred from the test surface to the cleaning product.

2. The method of claim 1, wherein the steps of rotating the cleaning product over the test surface and lifting the cleaning product away from the test surface occur simultaneously.

3. The method of claim 1, wherein the roller comprises a sleeve, the sleeve forming the outer surface of the roller, wherein the sleeve comprises a projection.

4. The method of claim 3, wherein the sleeve is a skin mimicking material.

5. The method of claim 3, wherein the sleeve comprises a compressible material.

6. The method of claim 1, wherein the controlled insult comprises a marker for visually quantifying the controlled insult transferred from the test surface to the cleaning product.

7. The method of claim 1, wherein the step of rotating the cleaning product over the test surface occurs after the step of moving the cleaning product in the machine direction over the controlled insult on the test surface.

8. The method of claim 1, wherein the test surface comprising a skin mimicking material, wherein the skin mimicking material is compressible.

9. The method of claim 1, wherein the controlled insult is an artificial soil.

10. The method of claim 1, wherein the cleaning product is a composition.

11. The method of claim 1, wherein the cleaning product is a substrate.

12. The method of claim 1, wherein the step of moving the cleaning product in the machine direction over the controlled insult comprises simultaneously applying pressure to the test surface.

13. The method of claim 12, wherein the pressure applied to the test surface is in the range of 0.1 to 10 psi.

14. The method of claim 1, wherein the step of moving the cleaning product in the machine direction over the controlled insult comprises moving the roller at a translational speed in the range of 0.1 to 2 cm/s.

15. The method of claim 1, wherein the step of rotating the cleaning product over the test surface comprises rotating the roller at a rotational speed in the range of 0.1 to 5 cm/s.

16. The method of claim 1, wherein the controlled insult is a first controlled insult, wherein the cleaning product is a first cleaning product, and further comprising the steps of:
- cleaning the test surface;
- applying a second controlled insult to the test surface;
- affixing a second cleaning product to the outer surface of the roller;
- positioning the second cleaning product into contact with the test surface;
- moving the second cleaning product in the machine direction over the controlled insult on the test surface;
- rotating the second cleaning product over the test surface;
- lifting the second cleaning product away from the test surface;
- measuring the amount of the second controlled insult transferred from the test surface to the second cleaning product; and
- comparing the amount of the second controlled insult transferred to the second cleaning product with the amount of the first controlled insult transferred to the first cleaning product.

* * * * *